US010825195B2

(12) United States Patent
Mech et al.

(10) Patent No.: US 10,825,195 B2
(45) Date of Patent: Nov. 3, 2020

(54) SPATIAL INDEX CREATION FOR IHC IMAGE ANALYSIS

(71) Applicant: HOFFMANN-LA ROCHE INC., Little Falls, NJ (US)

(72) Inventors: Franziska Mech, Berg-Aufhausen (DE); Angelika Fuchs, Munich (DE); Jan Kuentzer, Eurasburg (DE); Otto Huber, Iserlohn (DE); Alex Kohn, Penzberg (DE); Eckhart Guthoehrlein, Munich (DE)

(73) Assignee: Hoffman-La Roche, Inc., Little Falls, NJ (US)

( * ) Notice: Subject to any disclaimer, the term of this patent is extended or adjusted under 35 U.S.C. 154(b) by 210 days.

(21) Appl. No.: 16/091,245

(22) PCT Filed: Mar. 2, 2017

(86) PCT No.: PCT/EP2017/054917
§ 371 (c)(1),
(2) Date: Oct. 4, 2018

(87) PCT Pub. No.: WO2017/174267
PCT Pub. Date: Oct. 12, 2017

(65) Prior Publication Data
US 2019/0156510 A1 May 23, 2019

(30) Foreign Application Priority Data
Apr. 6, 2016 (EP) .................................... 16164102

(51) Int. Cl.
*G06T 7/73* (2017.01)
*G06T 7/00* (2017.01)
(Continued)

(52) U.S. Cl.
CPC ................ *G06T 7/73* (2017.01); *G06F 16/51* (2019.01); *G06K 9/0014* (2013.01);
(Continued)

(58) Field of Classification Search
CPC combination set(s) only.
See application file for complete search history.

(56) References Cited

U.S. PATENT DOCUMENTS

| 6,446,060 B1* | 9/2002 | Bergman | G06F 16/58 |
| | | | 707/770 |
| 2007/0025606 A1* | 2/2007 | Gholap | G06F 16/58 |
| | | | 382/128 |
| 2013/0338016 A1* | 12/2013 | McDonough | G01N 33/582 |
| | | | 506/8 |

FOREIGN PATENT DOCUMENTS

WO   WO-2015124772 A1   8/2015

OTHER PUBLICATIONS

Fusheng Wang et al: "High Performance Analytical Pathology Imaging Database for Algorithm Evaluation", Sep. 22, 2011 (Sep. 22, 2011), XP055188351, Retrieved from the Internet <URL:http://www.openpais.org/fushengwang/papers/HPDBValidation-CameraReady.pdf> [retrieved on May 8, 2015].
(Continued)

*Primary Examiner* — Zhiyu Lu
(74) *Attorney, Agent, or Firm* — Harness, Dickey & Pierce, P.L.C.

(57) ABSTRACT

An image analysis method for analyzing an IHC tissue sample includes storing, for each of one or more sets of digital images, a set-ID in a spatial database of a spatial DBMS, the images of each set depicting the same or adjacent layers of the IHC tissue sample; storing, for each of the, a plurality of spatial data objects in the database in association with the set-ID; creating, by the spatial DBMS, at least one spatial index covering the objects of the images
(Continued)

contained in the one or more sets; applying, by the spatial DBMS, a spatial database operation on the at least one spatial index for determining the relative positions of objects of two or more images of a selected set; and providing the relative positions as input for determining the distance and/or relative position of the biomedical features of the tissue sample.

15 Claims, 4 Drawing Sheets

(51) Int. Cl.
*G06T 7/50* (2017.01)
*G06T 7/30* (2017.01)
*G16H 30/20* (2018.01)
*G06F 16/51* (2019.01)
*G06K 9/00* (2006.01)
*G06K 9/62* (2006.01)
*G06T 7/60* (2017.01)

(52) U.S. Cl.
CPC ....... *G06K 9/00147* (2013.01); *G06K 9/6212* (2013.01); *G06T 7/0012* (2013.01); *G06T 7/30* (2017.01); *G06T 7/50* (2017.01); *G06T 7/60* (2013.01); *G16H 30/20* (2018.01); *G06K 2209/05* (2013.01); *G06T 2207/30024* (2013.01); *G06T 2207/30028* (2013.01); *G06T 2207/30096* (2013.01)

(56) References Cited

OTHER PUBLICATIONS

International Search Report PCT/ISA/210 for International Application No. PCT/EP2017/054917 dated Apr. 6, 2017.
Written Opinion of the International Searching Authority PCT/ISA/237 for International Application No. PCT/EP2017/054917 dated Apr. 6, 2017.
International Preliminary Report on Patentability for International Application No. PCT/EP2017/054917 dated May 16, 2018.

* cited by examiner

SPATIAL INDEX CREATION FOR IHC IMAGE ANALYSIS

CROSS-REFERENCE TO RELATED APPLICATIONS

This application is a national phase under 35 U.S.C. § 371 of PCT International Application No. PCT/EP2017/054917 which has an International filing date of Mar. 2, 2017, which claims priority to European Application No. 16164102.2, filed Apr. 6, 2016, the entire contents of each of which are hereby incorporated by reference.

FIELD OF THE INVENTION

The present invention relates to an image analysis system for analyzing images of IHC tissue samples.

BACKGROUND AND RELATED ART

A plurality of digital imaging solutions in pathology exist aiming at generating a large number of digital images of tissue samples and/or generating high-resolution images of whole slides. The processing of large numbers of digital images, in particular high resolution whole slide images, for diagnostic, educational, and research purposes may be highly complex and may consume a large amount of computational resources, in particular CPU and memory. Gains in computer processing power, data transfer speeds and cloud storage solutions have enabled the use of digital images for a wider variety of purposes in pathology, but still the processing and analysis of large numbers of digital images, in particular whole slide images, is a technological challenge that can often not be adequately solved with state of the art image processing techniques at reasonable costs.

The invention aims to provide an improved image analysis system and corresponding image analysis method.

SUMMARY OF INVENTION

The invention provides for an image analysis system for analyzing an IHC tissue sample, a corresponding image analysis method and database management system as claimed in the respective independent claims. Embodiments of the invention are given in the dependent claims. Embodiments of the invention can be combined freely with each other provided they are not mutually exclusive.

In one aspect, the invention relates to an image analysis method for analyzing an IHC tissue sample. The method comprises:
- storing, for each of one or more sets of digital images, a set-ID in a spatial database of a spatial DBMS, the digital images of each digital image set depicting the same or adjacent layers of the IHC tissue sample;
- storing, for each of the digital images, a plurality of spatial data objects in the spatial database in association with the set-ID, each spatial data object being a point, a line, a polygon or a combination thereof and representing a biomedical feature of the tissue sample;
- creating, by the spatial DBMS, at least one spatial index covering the spatial data objects of the digital images contained in the one or more sets;
- selecting one of the one or more sets of digital images;
- applying, by the spatial DBMS, a spatial database operation on the at least one spatial index for determining the relative positions of spatial data objects of two or more digital images of the selected digital image set;
- providing the relative positions as input for determining the distance and/or relative position of the biomedical features of the tissue sample represented by the spatial data objects of the two or more digital images.

Generating at least one spatial index for the spatial data records of one or more images of a tissue sample may be advantageous as it may now be possible to analyze spatial information of a plurality of biomedical features in a large number of digital IHC images, including whole slide images, in a highly efficient manner. Instead of using an application program for performing the analysis of the relative position of biomedical features, optimized spatial database operations are used that were originally designed for processing geodata, i.e., a completely different kind of data. Thus, data traffic to and from an application program for determining the relative position of different biomedical features in an image can be avoided. Moreover, by using spatial database operations on spatial data objects representing biomedical features instead of user-defined application program routines, speed-optimized routines that are adapted to quickly process a large number of spatial data objects can be used, thereby further reducing CPU and memory consumption.

According to embodiments, each of the spatial data objects is stored as a data record in a respective line of a table of the spatial database.

The digital images may be stored in a separate database and may be connected to the spatial data objects extracted therefrom and stored in the spatial database via the set-IDs. According to other embodiments, the digital images may also be stored in the spatial database.

Depending on the embodiment, the spatial index is selected from the group comprising:
an R-tree index (in an R-tree, the spatial data objects are grouped using a minimum bounding rectangle—MBR); R+ tree index; R* tree index; Hilbert R-tree index; a quadtree index; a Grid spatial index; a Z-order index; an UB-tree index; X-tree index; Kd-tree index; m-tree index; (an m-tree index can be used for the efficient resolution of similarity queries on complex objects as compared using an arbitrary metric); binary space partitioning (BSP-tree) index.

According to embodiments, the biomedical features of the tissue sample represented by the analyzed two or more data objects belong to at least two different types of biomedical features. For example, the at least two types are selected—in any combination—from a group comprising: a particular cell type, a particular organelle type, a cell cluster of a particular cluster type, a particular anatomical structure spanning multiple cells, a particular tissue type, a tumor tissue. For example, the relative distance and spatial distribution of tumor cells and non-tumor or lymphocyte cells could be determined for determining the degree of immune cell infiltration of a tumor tissue or for determining the degree of the tumor tissue infiltrating healthy non-tumor tissue. Alternatively, the occurrence and spatial distribution of a particular biomarker, e.g. a membrane protein, an epithelial protein, a cytosolic protein or a nuclear protein within a cell could be determined for classifying the cell type, e.g. classifying the cell type as biomarker-positive or biomarker-negative cell, as tumor or non-tumor cell, as a particular cell type, e.g. a regulatory T-cell or another type of T-cell, as liver cell, blood vessel cell, lung cell or apoptotic cell or the like. The detection of the relative location of biomedical features, e.g. of certain biomarkers may be used for identifying tissue-regions, tumor-regions, cell clusters and their boundaries, anatomical structures such as blood vessels, nerve cells, and the like.

This may be advantageous as the relative position and distribution of biomedical features may allow to automatically or semi-automatically compute a diagnosis or a suggestion for a diagnosis (e.g. of a tumor type and/or tumor stage) and/or to compute a suggestion for a suitable treatment. Said information may also be used for executing a classification operation using the relative position information as input, e.g. for classifying cells or organelles and optionally also highlighting features of different biomedical classes differently and overlaying the highlights over one of the digital images of the sample.

According to embodiments, an application program, e.g. an image analysis application program, automatically identifies one or more of the biological features in some or all of the digital images of the one or more sets. The identification comprises, for example, automatically performing a blob extraction and blob classification operation for automatically classifying pixel regions of the digital image representing a biological feature of a particular type. For example, a pixel blob may be identified by a variety of different methods, e.g. image segmentation, thresholding, or other image analysis techniques. A pixel blob may be classified as tumor cell or non-tumor cell or apoptotic cell etc. Likewise, edge-detection algorithms, classifiers, machine learning and/or statistical image analysis operations may be performed for identifying nuclei, cell boundaries or the like in the digital images. For example, the image analysis application program may access and read the digital images perform the blob identification, and store the identified biomedical features in the spatial database. In some embodiments, the spatial DBMS also detects some biomedical features in a digital image while an image analysis application program detects and stores other ones of the biomedical features.

In addition, or alternatively, the spatial DBMS receives one or more further ones of the biological features in some or all of the digital images of the one or more sets. The received further biological features are pixel regions of the digital image which have been manually classified as representing a biological feature of a particular type. For example, a pathologist may have manually classified a particular pixel blob as being a tumor cell and another pixel blob as being an apoptotic cell. The position information of said annotated pixel regions is provided as the further biomedical features to the spatial DBMS and is stored in the spatial DBMS.

According to embodiments, the spatial DBMS or an image analysis application program automatically extracts the spatial data objects from the automatically identified and/or manually classified biomedical features. For example, the DBMS or the application program may analyze the pixel intensities or other image attributes of blobs and regions corresponding to the biomedical features and may representing them as polygons, lines and/or points. For example, complex anatomical structures such as the outlines of blood vessel walls, a cluster of cells or a tissue region may be represented as polygons, individual cells or nuclei may be represented as polygons or points and/or cell membranes or tissue boundaries may be represented as lines. Said extracted spatial data objects are then stored in the storing step in the spatial database. Typically, the extracted spatial data objects are stored in association with the digital images from which the objects were derived.

The extraction of the polygons, lines or points may be performed by an application program. This may have the advantage that typically an application program is more flexible and a large variety of algorithms for extracting spatial data objects may be implemented. Thus, depending on the biomedical question to be answered, different spatial data objects may be extracted from the same digital image. For example, a particular blob representing a tumor cell of a particular type may be represented by a polygon (e.g. if the size is relevant and shall be estimated later) or as a point in a 2D coordinate system.

According to embodiments, the method comprises creating, for each of the digital images of each of the one or more sets of digital images, a respective spatial index or a respective partition of the at least one spatial index. The spatial index or index partition created for a particular digital image covers the spatial data objects derived from and contained in said digital image.

This may decrease the amount of data that is loaded into memory for performing a database operation on a plurality of digital images.

According to alternative embodiments, the method comprises creating, for each of the digital image sets a respective spatial index or a respective partition of the at least one spatial index. The spatial index or index partition created for a particular digital image set covers the spatial data objects derived from and contained in all digital images of said set.

Creating set-based partitions may have the advantage that the sets represent a set of biologically related data. Defining set-based indices or partitions may allow to selectively load spatial data objects into memory that are candidates for being processed by a spatial data operation for identifying spatial relations of biomedical features relating to the same tissue sample or region of a tissue sample.

In addition, or alternatively, the method comprises creating, for each of the at least two different types of biomedical features of each of the one or more sets of digital images, a respective spatial index or a respective partition of the at least one spatial index. The spatial index or index partition created for a particular biomedical feature and a particular image set covers all spatial data objects in all of the digital images of said particular set which represent said type of biomedical feature.

For example, a first digital image may comprise a plurality of polygons respectively representing cells expressing a particular biomarker which may indicate that said cells are tumor-cells. A second digital image of the same selected image set may represent immune cells.

By representing polygons representing tumor-cells in a different spatial index or in different partitions of the at least one spatial index than polygons representing immune cells, spatial database operations may be accelerated as the number of data objects (corresponding to the size of the index or index partition) loaded into memory for performing a spatial operation may be reduced. For example, the index may comprise a first partition for spatial objects representing tumor cells of a particular image set, a second partition for spatial objects representing immune cells in said particular image set, a third partition for spatial objects representing blood vessel cells, . . . , and an nth partition for spatial objects representing apoptotic cells.

In case the relative position of tumor cells and immune cells has to be evaluated, the partition corresponding to the apoptotic cells may not have to be loaded into memory. In case the relative position of tumor cells and apoptotic cells has to be evaluated, the partition corresponding to the immune cells may not have to be loaded into memory.

Creating additional partitions and/or indices according to embodiments of the invention may be advantageous as the memory consumption and/or CPU consumption may be reduced: it has been observed that creating a spatial index for the spatial data objects of a particular image or image set provides for a very good compromise regarding index size (the smaller the index, the smaller the amount of data to be loaded into memory) and index coverage (the smaller the index, the higher the handling costs for managing and accessing multiple indices in order to be able to process a request) for many database queries relating to the assessment of spatial proximity of two or more different biomedical features of a tissue sample. In addition, feature-based or feature-and-image-set based spatial indices or partitions may be used for further reducing the memory consumption for several types of database queries.

According to embodiments, the image-based and the feature-type-based index creation or index partitioning may be combined. For example, n+m spatial indices or n+m spatial index partitions are created in case a first image comprises biomedical features of n different types and a second image comprises biomedical features of m different types.

In effect, a highly flexible and memory-saving method for analyzing the relative position of image features of IHC images may be provided which can be used for a plurality of different biological or medical questions and use case scenarios.

According to embodiments, the method comprises performing a pre-processing operation before performing the analysis of the relative positions of the spatial data objects. The preprocessing comprises the spatial DBMS automatically pre-computing the area size, the geometric center and/or the minimum bounding rectangle ("mbr") of the spatial data objects of the digital images. The precomputed area size, geometric center and/or the minimum bounding rectangle may be stored to the spatial database or to another form of non-volatile data storage. The spatial DBMS and/or an image analysis application program uses the precomputed area size, geometric center and/or the minimum bounding rectangle as input for determining the distance and/or relative position of the biomedical features.

This may be advantageous as the computation of the area size, the geometric center and/or the mbr are computationally demanding tasks, in particular if performed for several 10.000 or even 100.000 of spatial data objects per image. By pre-computing and storing the above mentioned features, the resulting information may be re-used multiple times for different biomedical questions, e.g. for comparing the size of non-tumor tissue with tumor tissue, for determining the size of cells for performing a later cell classification operation, determining the geometric center of tissue regions for providing input feature for a classifier to be applied later on the image data and so on. The pre-computation may at least partly or completely be performed by using spatial database operations provided by the spatial DBMS.

For example, an Oracle Database comprising the "Oracle® Spatial component" may be used as the spatial DBMS. This type of DBMS comprises spatial database routines for managing geographic and location-data in a native type. It supports a "SDO_GEOM" data type that can be used for storing the spatial data objects and supports a plurality of spatial database operations capable of processing the SDO_GOEM data type. For example, the SDO_GEOM.SDO_AREA operation computes the area of a two-dimensional polygon. The SDO_GEOM.SDO_MBR returns the minimum bounding rectangle of a spatial data object or of an aggregation of spatial data objects. The SDO_GEOM.SDO_CENTROID operation returns the centroid of a polygon.

According to some embodiments, each digital image of the selected set of digital images is derived from a respective one of a plurality of adjacent layers of a tissue sample. For example, the different layers may be stained differently for identifying different biomarkers, e.g. by using a first antibody with a first fluorescent stain for selectively identifying a first biomarker and by using at least a second antibody with a second fluorescent stain for selectively staining a corresponding second biomarker. As the layers are adjacent, it can safely be assumed that although the fluorescent signals of the first and second stain are not derived from the same tissue layer, the relative position of the first and second biomarker can be identified by comparing intensity signals of the first and second stain. Thus, in this embodiment, each digital image of an image set may correspond to a respective tissue layer and may correspond to a respective biomarker and stain. One or more of said images may also correspond to a generic stain, e.g. hematoxylin and/or eosin, used for identifying tissue areas vs. glass-areas of the tissue slide.

According to embodiments, an image analysis application program generates each of the sets of digital images. The generation comprises performing an image registration operation for registering a plurality of digital images depicting the same or adjacent layers of an IHC tissue sample into a common coordinate system.

For example, the image analysis program may perform a spectral unmixing operation for generating the plurality of digital images depicting the same layer of an IHC tissue sample. Each of the digital images of the at least one set corresponding to a different color. Thus, by applying spectral unmixing (also referred to as color deconvolution), it is possible to generate a set of digital images for a particular layer from a single multi-channel image depicting the layer of the tissue sample. For example, international patent application WO 2015/124772 which is hereby incorporated in its entirety in the present disclosure describes a system for image unmixing using group sparsity modeling. The color deconvolution approaches described in said international patent application are used by embodiments of the invention for generating the one or more sets 113 of digital images whose images depict (different spectral components of) the same tissue sample layer.

According to embodiments, set-IDs of multiple sets of digital images and the corresponding spatial data objects are stored in the spatial database.

One or more first ones of the digital image sets respectively comprise digital images of a tumor biopsy sample before treatment.

One or more second ones of the digital image sets respectively comprise digital images of a tumor biopsy sample during treatment.

In addition, or alternatively, one or more third ones of the digital image sets respectively comprise digital images of a tumor biopsy sample after treatment.

The method may comprise determining the relative position of spatial data objects representing two or more different biological features for each of the first, second and third digital image sets. Then, optionally, the DBMS or an image analysis application program may compare the relative positions of biomedical features computed for the first, second and/or third image sets for determining differences in treated vs. currently treated or previously treated patients. For example, a statistical test may be performed for comparing the relative positions. This may be advantageous as a comparison of the relative position of two or more biomedical features in a plurality of untreated, currently treated and previously treated persons is enabled that can be performed quickly even for large numbers of patients.

According to embodiments, at least the set-IDs and the spatial data objects of a plurality of sets of digital images are stored in the spatial database. Fourth ones of the sets of digital images comprise digital images of tissue samples of a first cohort of people who have a particular condition. Fifth ones of the sets of digital images comprise digital images of tissue samples of a second cohort of people who do not have particular condition. The spatial DBMS selects the fourth sets and the fifth sets of the digital images and performs the analysis on each of the fourth and fifth sets of digital images. The analysis results are stored. Then, the spatial DBMS or an image analysis application program computes a first statistical mean of the relative position of spatial data objects representing two or more different biological features of the digital images in the fourth digital image sets. In addition, the spatial DBMS or the image analysis application program computes a second statistical mean of the relative position of spatial data objects representing said two or more different biological features of the digital images in the fifth digital image sets. Then, the spatial DBMS or the image analysis application program automatically compares the first and second statistical means for identifying statistically significant differences between the first and the second cohort of persons. A "cohort" as used herein is a group of people having similar life histories, age, health status, education, dietary habits or the like and/or have a similar health status, e.g. having or not having a condition.

In a further beneficial aspect, using spatial database operations for comparing the spatial relation of biomedical features e.g. in samples of treated vs. untreated patients or in tissue samples of different cohorts, it is possible to generate standardized and reliable diagnostic or educative results. This was not possible when using manual image analysis techniques as e.g. the manual assessment of the distance of features by different pathologists or even the same pathologists on different days may prohibit a comprehensive and accurate comparison of image data acquired for a plurality of tissue samples.

According to embodiments, the spatial database operation for analyzing the relative position of the spatial data objects is selected from a group comprising:
  determining if a first region of one of the digital images in the selected set is completely contained in a second region of another digital image of the same set;
  determining if a first region of one of the digital images in the selected set overlaps with a second region of another digital image of the same set;
  determining the spatial distance of a spatial data object representing a biological feature of a first type in one of the digital images in the selected set relative to a spatial data object representing a biological feature of another type in another one of the digital images of the same set; for example, the Oracle Spatial operation SDO_GEOM.SDO_DISTANCE may be used for computing the distance between two spatial objects;
  determining patterns of relative locations of spatial data objects representing a biological feature of a first type in one of the digital images in the selected set relative to the location of spatial data objects representing a biological feature of another type in another one of the digital images of the same set.

Embodiments of the invention may be particularly advantageous in the context of large scale cohort studies as a plurality of persons may contribute one or more digital images and a large amount of data needs to be analyzed quickly.

According to embodiments, the spatial DBMS computes the density of spatial data objects of one or more of the digital images of one or more of the digital image sets. Preferentially, the spatial DBMS uses inbuilt spatial operations for quickly performing the density calculation. Then, the DBMS or an image analysis program analyzes the computed densities for automatically classifying the spatial data objects into one of a plurality of predefined biomedical feature classes, e.g. into a particular cell type or tissue type, into a particular T-cell subclass like cytotoxic T-cells vs. regulatory T-cells etc.

In a further aspect, the invention relates to a non-volatile computer-readable storage medium. The storage medium comprises computer-readable instructions that, when executed by a processor, cause the processor to perform a method according to any one of the previous claims.

In a further aspect, the invention relates to an image analysis system comprising a spatial DBMS with a spatial database and comprising a processor. The processor is configured for:
  storing, for each of one or more sets of digital images, a set-ID in a spatial database of a spatial DBMS, the digital images of each digital image set depicting the same or adjacent layers of the IHC tissue sample;
  storing, for each of the digital images, a plurality of spatial data objects in the spatial database in association with the set-ID, each spatial data object being a point, a line, a polygon or a combination thereof and representing a biomedical feature of the tissue sample;
  executing first program routines of the spatial DBMS for creating at least one spatial index covering the spatial data objects of the digital images contained in the one or more sets;
  receiving a selection of one of the one or more sets of digital images;
  executing second program routines of the spatial DBMS for applying a spatial database operation on the at least one spatial index for determining the relative positions of spatial data objects of two or more digital images of the selected digital image set and for providing the relative positions as input for determining the distance and/or relative position of the biomedical features of the tissue sample represented by the spatial data objects of the two or more digital images.

In a further aspect, the invention relates to a spatial database management system comprising:
  a spatial database comprising:
    at least set-IDs of one or more sets of digital images, the digital images of each digital image set depicting the same or adjacent layers of an IHC tissue sample;
    for each of the digital images, a plurality of spatial data objects, each spatial data object being a point, a line, a polygon or a combination thereof and representing a biomedical feature of the tissue sample;
  first program routines for creating at least one spatial index covering the spatial data objects of the digital images contained in the one or more sets; and
  second program routines for applying a spatial database operation on the at least one spatial index for determining the relative positions of spatial data objects of two or more digital images of a selected one of the one or more digital image sets and for providing the relative positions as input for determining the distance and/or relative position of the biomedical features of the tissue sample represented by the spatial data objects of the two or more digital images.

A "spatial database management system" or "spatial DBMS" as used herein is a software application designed to allow the definition, creation, querying, update, and administration of spatial databases.

A "spatial database" or "geodatabase" as used herein is a database that is optimized to store and query data that represents objects defined in a geometric space. A spatial database allows representing simple geometric objects such as points, lines and polygons and optionally also more complex structures such as 3D objects, topological coverages, and/or linear networks. While typical databases are designed to manage various numeric and character types of data, spatial databases comprise additional functionality for processing spatial data objects efficiently.

Spatial data objects may also be referred to as "spatial primitives" or "simple geometric objects". The term "geometry" may be used to refer to individual spatial data objects and for aggregations of spatial data objects.

A "spatial database operation" as used herein is a database routine that is configured for analyzing spatial information of one or more spatial data objects. The spatial database operations are typically speed-optimized to efficiently process the spatial data objects by using a spatial index created for a plurality of spatial data objects. For example, a spatial database may support one or more of the following spatial database operations: spatial Measurements (e.g. computing the line length, the area of a polygon, the distance between spatial data objects), spatial functions (modifying existing spatial data objects to create new ones, for example by providing a minimum bounding rectangle around them, intersecting spatial data objects, merging spatial data objects); spatial predicates (performing true/false queries about spatial relationships between spatial data objects for checking e.g. if polygons overlap or are within a maximum distance from another spatial data object), and others.

A "spatial index" as used herein is a data structure used by spatial databases to optimize spatial queries. Spatial index types typically handle spatial queries (such as how far two points differ, or whether points fall within a spatial area of interest, whether two polygons specify disjoint, intersecting, overlapping or touching areas) more efficiently than conventional indices.

A "tissue sample" as used herein is a piece of tissue derived e.g. from a biopsy or is a set of cells including blood cells taken from an organism, e.g. a human or other mammal. For example, the tissue sample or a slice thereof may be stained using immunohistochemical (IHC) staining protocols.

The term "digital image" as understood herein encompasses raw image data acquired from the biological tissue sample, such as by means of an optical sensor or sensor array, or pre-processed image data. In particular, the image data may comprise a pixel matrix and/or may be a pixel matrix derived from a spectral unmixing (color deconvolution) operation.

A "biomarker" as used herein is a property of a tissue sample (e.g. (a presence of) a particular cell type, for instance immune cells), in particular a tissue property indicative of a medical condition. The biomarker may be identifiable by the presence of a particular molecule, for instance a protein, in the tissue sample.

A "biomedical feature" as used herein is a biomedical property of a tissue sample obtained by automatically analyzing and/or manually annotating a digital image of the tissue sample. For example, a digital image may comprise pixel intensity information being indicative of the presence and amount of a particular biomarker, molecule or cell structure. Said information may be used as input by a segmentation, blob detection or classification algorithm or may be evaluated by a human for assigning a biomedical attribute to respective pixels of the image. Said attributes or properties can be a class label that indicates that a set of pixels represents a cell (and not a glass slide background) or represents a particular organelle or a particular cell type.

A "set-ID" as used herein is an identifier that uniquely identifies a set of digital images in a database.

BRIEF DESCRIPTION OF THE DRAWINGS

In the following embodiments of the invention are explained in greater detail by way of example only making reference to the drawings in which.

DETAILED DESCRIPTION

Figure 1:
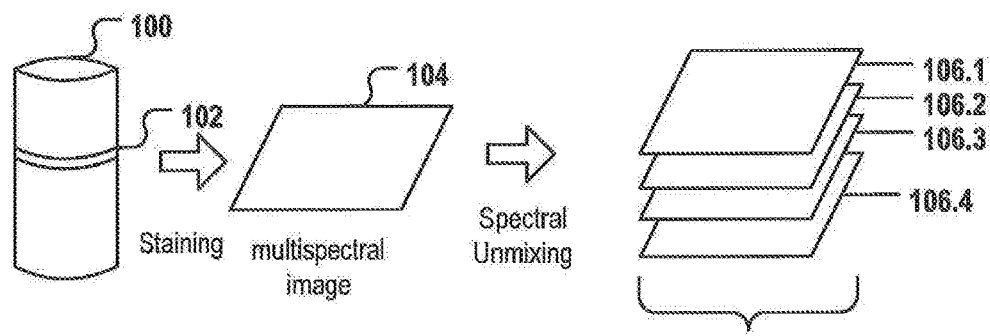
FIG. 1 shows the creation of a set of digital images of the same tissue sample layer.

FIG. 1 shows the creation of a set 112 of digital images 106.1-106.4 of the same layer 102 of a tissue sample 100. For example, as part of the diagnosis of many cancer types, e.g. colorectal cancer, one or more biopsy samples are taken. The biopsy sample is sliced into one or more thin tissue layers 102. The layer 102 may be stained with one or more stains selectively staining specific biomarkers, cells and/or organelles, and a multispectral image 104 is taken from one layer 102 to capture meaningful biomedical features that may allow to classify the tumor, provide a prognosis and/or a treatment suggestion. The multispectral image may comprise spectral information of a plurality of different stains, e.g. fluorescent stains, and/or may cover a whole slide comprising the layer 102. Thus, the resulting multispectral image is often very large. By applying a spectral unmixing procedure, a plurality of digital images 106-1-106.4 is created. Each of the images in set 112 may correspond to the intensity signals selectively generated by a respective stain and thus may correspond to a particular biomedical feature, e.g. the presence and distribution of a particular biomarker. Each of the images 106.1-106.4 may be processed and analyzed by an image analysis program using different techniques for automatically identifying biomedical features, e.g. tumor cells, immune cells, and so on, and for representing the identified biomedical features as spatial data objects, e.g. polygons, points or lines. The image analysis program stores the spatial data objects in a spatial database. For example, the automated biomedical feature detection may comprise blob identification, edge detection, segmentation, thresholding, the extraction of local intensity order patterns and other techniques. Various approaches and classifiers such as Support Vector Machines, neural networks or random forests may be applied on the biomedical features of the different types and/or for extracting the spatial data objects representing the biomedical features from each of the images. In sum, the images in set 112 comprise information on different biomedical features of the same single tissue slide layer 102.

Figure 2:
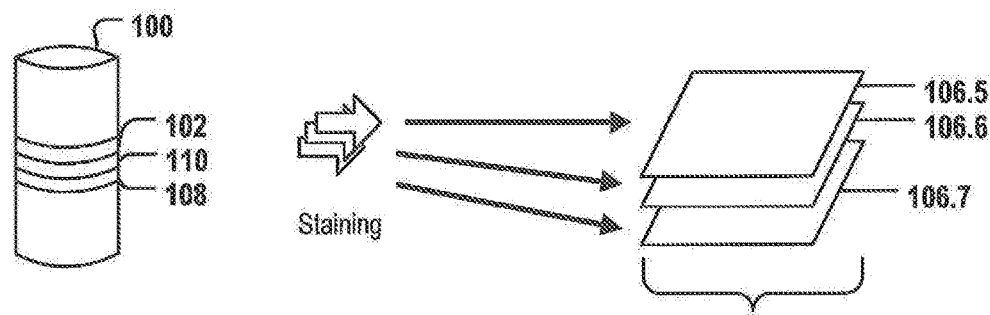
FIG. 2 shows the creation of a set of digital images depicting adjacent layers of a tissue sample.

FIG. 2 shows the creation of a set 113 of digital images 106.5-106.7 depicting adjacent layers 102, 108, 110 of a tissue sample. The biopsy sample is sliced into two or more thin tissue layers 102, 108, 110. Each tissue layer may be stained with a different staining protocol for selectively staining specific biomarkers, cells and/or organelles, and may be transferred on a respective slide. From each of the tissue slides comprising one of the layers, a respective image, typically a monochrome image 106.5-106.7 is taken, e.g. by a fluorescence microscope, a bright field microscope, a slide scanning apparatus or the like. Each of the images of the image set 113 capture meaningful biomedical features that may allow to classify the tumor, provide a prognosis and/or a treatment suggestion. As for the example depicted in FIG. 1, the images may be whole slide images and thus may often be very large. Each of the images in set 113 may correspond to the intensity signals selectively generated by a respective stain for a respective layer and thus may correspond to a particular biomedical feature, e.g. the presence and distribution of a particular biomarker. Each of the images 106.5-106.7 may be processed and analyzed by an image analysis program and/or routines of a spatial DBMS using different techniques as described already for FIG. 1. In sum, the images in set 113 respectively correspond to different adjacent layers of the tissue sample and respectively comprise information on different biomedical features.

Figure 3:
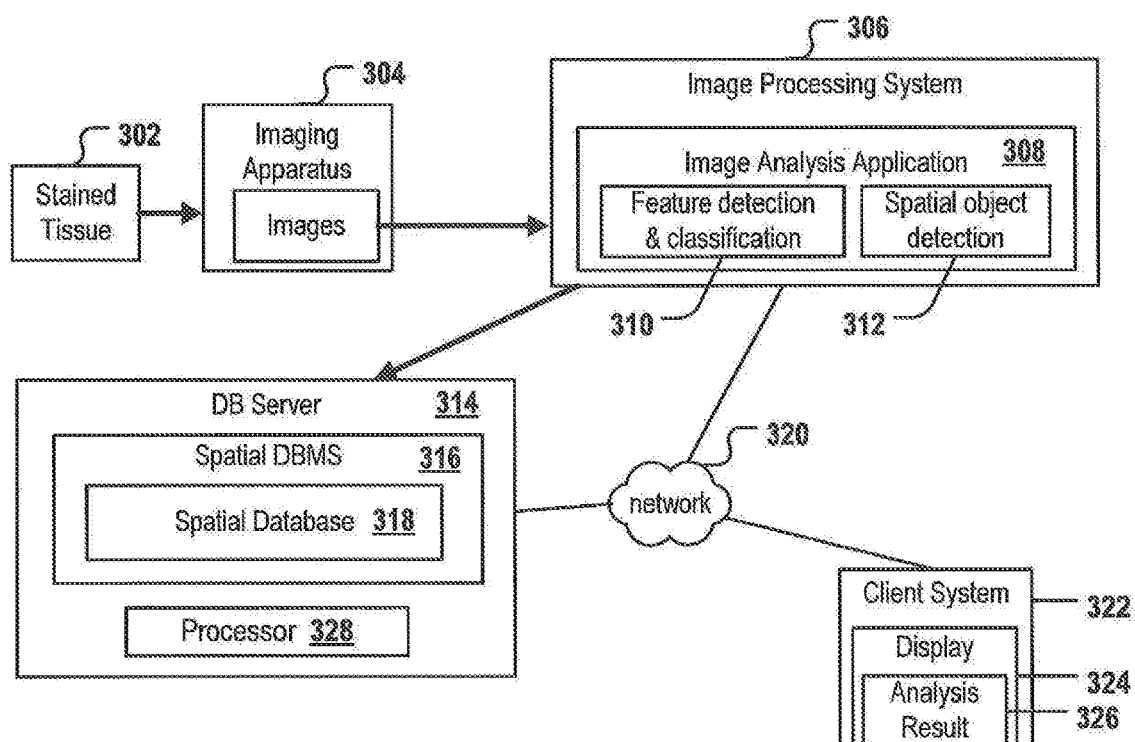
FIG. 3 shows a distributed system comprising a spatial DBMS.

FIG. 3 shows a distributed system comprising a spatial DBMS 316. The spatial DBMS is hosted on a database server 314 comprising a processor 328, a main memory and a non-volatile storage medium and comprises one or more spatial databases 318. The database server may be implemented as a cloud-based database system.

Optionally, the system may further comprise an image analysis program 308 hosted on an image processing system 306, e.g. a standard computer system, a user computer or an application server computer system. The image analysis application program 308 may comprise a feature detection and classification module 310, e.g. for automatically identifying biomedical features such as nuclei, cells, background regions, tissue borders and cells and for classifying said biomedical features, e.g. into tumor-cells and non-tumor cells. In addition, the image analysis application 308 comprises, according to embodiments, a further module 312 for detecting spatial objects representing the biomedical features. This module may use the biomedical features and/or the digital images said features were derived from as input for identifying spatial data objects, e.g. points, lines and polygons that represent said biomedical features. For example, the outline of a cell of a particular type (selectively identifiable via the stain whose intensity signal is depicted in a particular digital image) may be represented as a polygon. The generated spatial data objects are then stored in the spatial database. The spatial data objects derived from the respective images are stored in the spatial database 318 and used by speed-optimized spatial database operations later for determining the spatial distribution and relation of biomedical features.

The image processing system 306, e.g. a server or a standard computer, can be connected with the database server 314 via a network 320, e.g. the internet or the intranet.

According to some embodiments, the system is connected via the network 320 to one or more client computer systems 322 comprising a display. The client computer can be a computer assigned to a user, e.g. a pathologist or an immunologist. The computer 322 can be a desktop computer, a notebook, a tablet computer or a mobile battery powered telecommunication device, e.g. a smartphone. A user may submit a request via a client application program to the spatial database for determining, preferentially in a real-time mode, the distance and/or relative spatial location of two or more biomedical features identified in respective digital images in a set of biologically related images. The results 326 of this analysis are displayed to the user on a display 324 of the client device.

In addition, the system can comprise or be operatively coupled to an imaging apparatus 304, e.g. a slide scanner or a microscope that is configured for taking or scanning one or more images of one or more layers of a stained tissue sample 302. The (tissue) imaging apparatus 304 may for example comprise a bright-field illumination module that effects bright-field illumination of the tissue sample and may effect capture of the plurality of pixels representative of an image of the tissue sample during bright-field illumination of the tissue sample. In addition or alternatively, the (tissue) imaging apparatus 304 may comprise a CCD camera, e.g. a CCD camera selected from the group consisting of an RGB CCD camera and a CCD camera having multiple color channels. The (tissue) imaging apparatus may effect imaging, i.e. capture of the plurality of pixels representative of an image of the tissue sample, by means of a CCD camera selected from the group consisting of an RGB CCD camera and a CCD camera. For example, the CCD camera may capture pixels in each of a red, green and blue channel or in each of a red, green, blue and UV channel. The CCD camera may comprise a beam splitter for splitting incident light into the various (color) channels for capture.

The imaging apparatus 304 may store the generated digital images directly in the spatial database or may forward the images to the image processing system 308 for performing the feature and spatial data object extraction and for storing the images and the resulting spatial data objects in the spatial database 318. According to embodiments, one or more sets of images may comprise an RGB image and/or a CYMK image and/or monochromatic images derived from a multi-channel color image (an image comprising two or more (color) channels). As such, each pixel of some images may comprise color information for any of a plurality of color channels, e.g. for each of a red, green and blue channel of an RGB image. The color information may be stored in the spatial database in association with the x-y-coordinates of spatial data objects extracted later from the digital images in an image analysis procedure.

The spatial database comprises at least one spatial index that covers the spatial data objects of all images contained in one or more sets of images. In some embodiments, one spatial index (or partition) per image set or even per image is created. In some further embodiments, one spatial index (or partition) per biomedical feature is created and according to still further embodiments, a spatial index (or partition) per combination of biomedical feature and image or per combination of biomedical feature and individual image is created. In some embodiments, the partitions are stored in different physical table spaces for increasing performance. The spatial DBMS updates the spatial index or indices each time a new spatial data object is stored in the database for ensuring that the index is kept up to date.

According to embodiments, the spatial database operations operating on the spatial index of the spatial data objects implement a two-step inquiry model to perform database queries and joins: The two steps comprise a primary and secondary filter operation.

In the first filter operation, a (quick) selection of all candidate spatial data objects that meet an approximate, geometric boundary are identified. Said identification consists of geometric operations that use the spatial index for determining if a particular spatial data object or parts thereof fit within the approximate geometric boundary. For example, a minimum bounding rectangle or a minimum bounding ellipse of one or more of the spatial data objects may be computed as approximate geometric boundaries. Said approximate geometric boundaries are used for building up the spatial index, e.g. an R-tree or a linear quadtree.

In the secondary filter operation, the spatial DBMS compares only the ones of the candidate spatial data objects meeting the geometric requirements imposed by the primary filter operation. The secondary filter applies exact calculations on the result set from the primary filter to returns an exact result. The secondary filter typically requires more computational effort, but the exact calculation is no longer applied to all spatial data records, but only on a limited amount. Thus, while the primary filter is carried out only on the spatial index for providing a set of candidate data objects, the secondary filter is used for determining the exact spatial relationship between spatial objects based on the exact geometric positions and boundaries of the spatial data objects.

According to embodiments, at least some of the spatial database operations merely comprise a primary but not a secondary filter operation.

A plurality of stains may be coupled to antibodies or other molecules for specifically staining a respective particular biomarkers or other molecule. The color of each stain used in a staining protocol for staining one or more slices of a tissue sample may be unique so each stain color may correspond to a biomarker or other type of molecule.

For example, an antibody-coupled stain may have an affinity to at least one tissue feature selected from the group consisting of a tumor cell cytokeratin, a regulatory T-cell nucleus, a universal nucleus, a B-cell membrane, a universal T-cell membrane, and a cytotoxic T-cell membrane.

Figure 6:
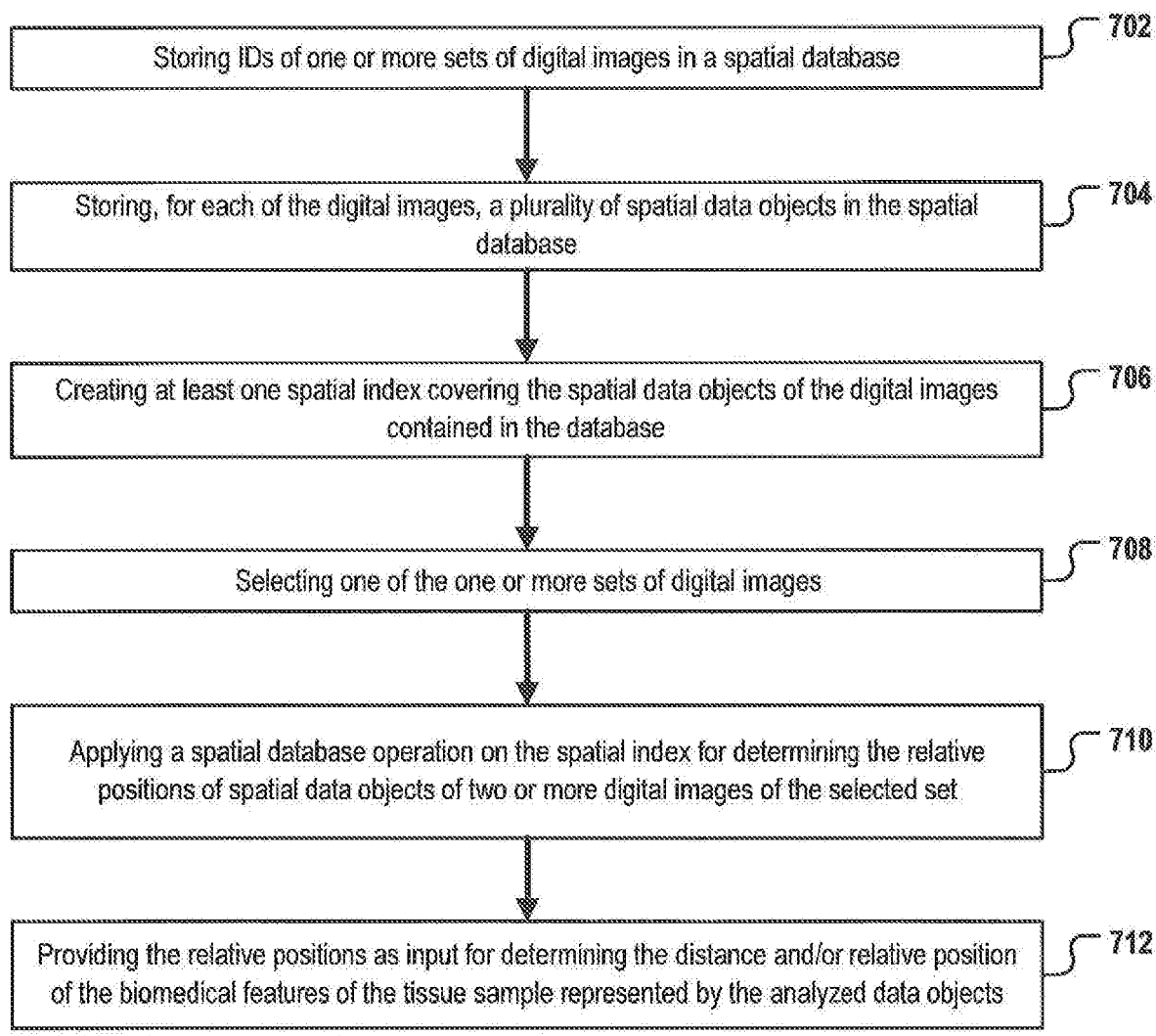
FIG. 6 is a flow chart of a method according to an embodiment of the invention.

FIG. 6 is a flow chart of an image analysis method for analyzing an IHC tissue sample 100 according to an embodiment of the invention that may be implemented by a system depicted in FIG. 3. For example, the sample 100 can be a colon cancer biopsy sample. One or more sets 112 113 of digital images 106.1-106.4; 106.5-106.7 are used by an image application program for extracting biomedical features and spatial data objects representing the biomedical features. The digital images of each digital image set depict the same 102 or adjacent layers 102, 110, 108 of the IHC tissue sample. For example, the image analysis application 308 may receive the images from the imaging apparatus 304, optionally perform a spectral unmixing operation, and store the received or generated digital images in an image management database. In addition, the image analysis application may alone or in interoperation with the spatial DBMS perform some image analysis steps, e.g. segmentation or blob identification for extracting biomedical features in the individual images and for representing the biomedical features as points, lines and/or polygons which are referred herein as "spatial data objects". Each spatial data object comprises at least one point having an x-coordinate value and an y-coordinate value. Lines and polygons comprise multiple x-y-value pairs which are connected to each other via an edge. A polygon is a 2-dimensional shapes made of straight lines, whereby the shape is "closed" (all the lines connect up).

In a first step 702, identifiers ("set-IDs") of the image sets are stored in a spatial database 318 of a spatial DBMS 316 for linking data records associated with the set-IDs to the original images stored in the image management database. In step 704, for each of the digital images, the spatial data objects are stored in the spatial database. The storing steps 702 and 704 may be triggered, for example, by the image analysis application program and may be performed repeatedly for a plurality of image sets obtained for respective tissue samples.

In step 706, the spatial DBMS creates for each of the sets of digital images, one spatial index covering the spatial data objects of the digital images contained in said set. In step 708, one or more of the sets of digital images is selected. For example, a user may perform the selection via an interface or the spatial DBMS may automatically select all image sets to be used for a spatial feature analysis. In step 710, the spatial DBMS applies a spatial database operation on the spatial index created for said selected digital image set. For example, INTERSECT or IS-CONTAINED-IN queries may be processed on the spatial index and/or densities of biomedical features represented by a set of spatial data objects may be computed for determining the relative positions of spatial data objects of two or more digital images of the selected digital image set and/or for obtaining feature density information. In step 712, the spatial DBMS provides the computed relative positions as input for a suitable image analysis routine for determining the distance and/or relative position of the biomedical features of the tissue sample represented by the spatial data objects of the two or more digital images. For example, the results generated in step 714 may be stored in a table of the spatial database that is accessible to the image analysis application program 308 or to a statistical application program. Alternatively, the spatial DBMS may comprise suitable program routines, e.g. some stored procedures, for performing the determination of the distance and/or relative positions.

Figure 4:
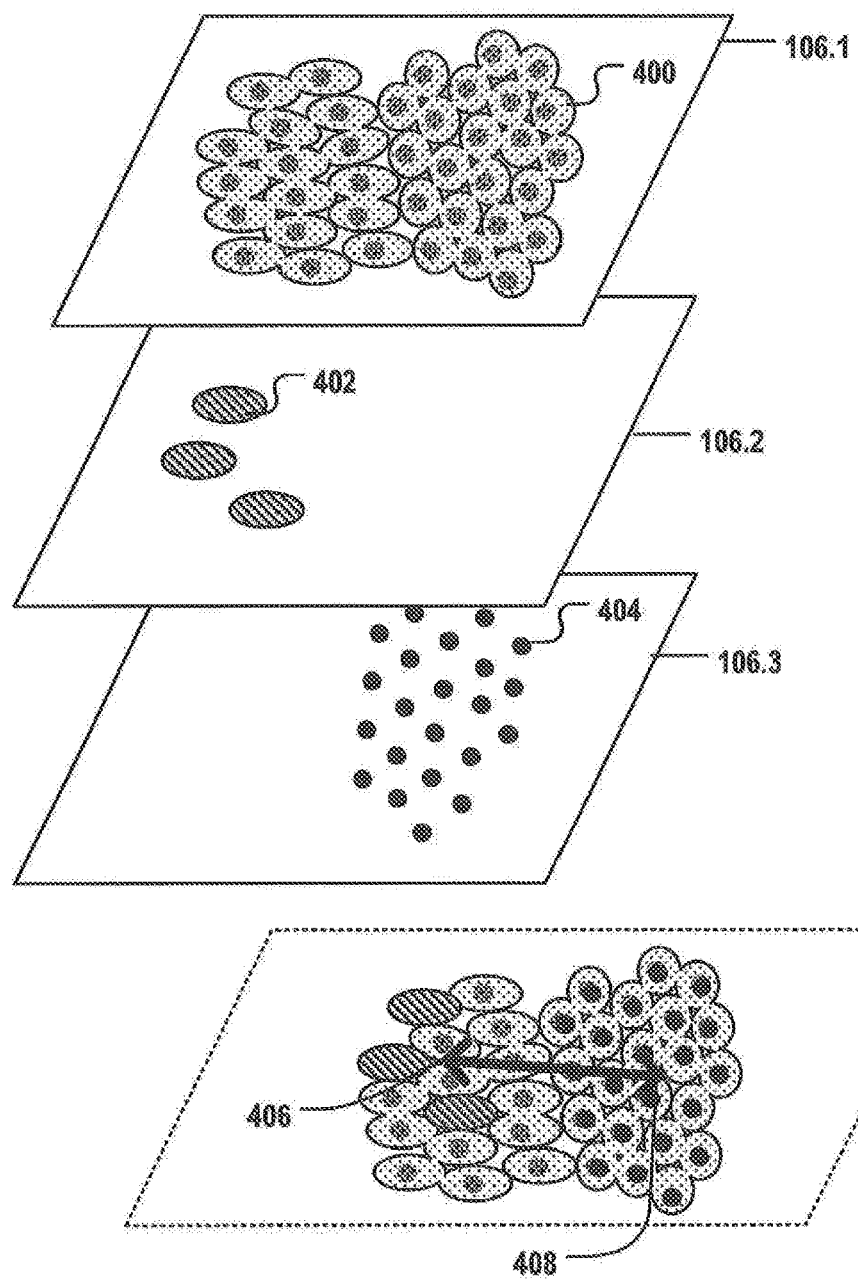
FIG. 4 depicts individual images of a digital image set.

FIG. 4 depicts individual images of a digital image set 112 in greater detail. Image 106.1 shows a plurality of cells 400 stained with hematoxylin and eosin (H&E). The nuclei have a darker color than the cytosolic portions of the cells. Image 106.2 shows three dots corresponding to a stain that specifically binds to a particular type of immune cell. Thus, dots 402 represent three immune cells having invaded tissue region 400. Image 106.3 shows a plurality of black dots 404 caused by the signal of a stain that specifically binds to a tumor marker. Thus, by performing an image analysis for e.g. dot detection, segmentation, thresholding and applying a classifier, it may be possible to extract one or more biomedical features from the individual tissues.

The dotted box below does not represent a digital image but illustrates that by combining the information contained in the multiple digital image, relevant biological features and their relative spatial location can be derived.

For example, the image shows that the right half of the tissue region 400 (the cells comprising the black dots 404) are tumor cells, the left half of the tissue regions consists of non-tumor cells. Moreover, it can be inferred that the three immune cells 402 have not invaded the tumor region. The spatial DBMS comprises spatial database operations e.g. for computing a minimum bounding rectangle, computing the geometric center of such a rectangle or of a polygon constituting a spatial data object, and determining the distance e.g. of the two geometric centers of two different biomedical features. For example, the distance between geometric center 406 of the immune cells 402 and the geometric center 408 of the tumor cells 404 can be determined quickly for 100.000 or more spatial objects and for many hundred or thousand image sets (e.g. in large cohort studies) very quickly and often even in real time. This may be achieved by pre-computing several spatial properties of biomedical features, e.g. the size or geometric centers of tissue regions, cell clusters, cells or the like and using speed-optimized spatial database operation for computing derivative spatial information, e.g. the distance between individual cells of different types or the distance between the geometric mean of sets of different cell types. The distance between the geometric centers 406 and 408 of immune cells and tumor cells is indicated in FIG. 4 by the arrow. However, this way of computing a relative position of two biomedical features (immune cells and tumor cells) is just an example. Depending on the biomedical question, other types of biomedical features, other distance measures and other types of spatial database operations may be used.

FIG. 5 depicts multiple biomedical use case scenarios for performing spatial database operations on multiple digital images of an image set. FIG. 5a depicts a tissue slide 600 comprising a sample slice with multiple cells. The region 602 corresponds to the glass, the left portion 602 will later be identified as non-tumor cells and the right portion 606 of the cells will later be identified as tumor cells. Each cell may be represented as multiple polygons: a first polygon may represent the cell membrane 612 surrounding cytosolic regions 608 and thus represents the outline of the cell. A second polygon may represent the cell nucleus 610. The cell membrane and the nucleus may have been automatically identified by applying an image analysis method on an H&E stained image or on any other type of digital image comprising sufficient information on cellular and nuclear boundaries.

Figure 5A:
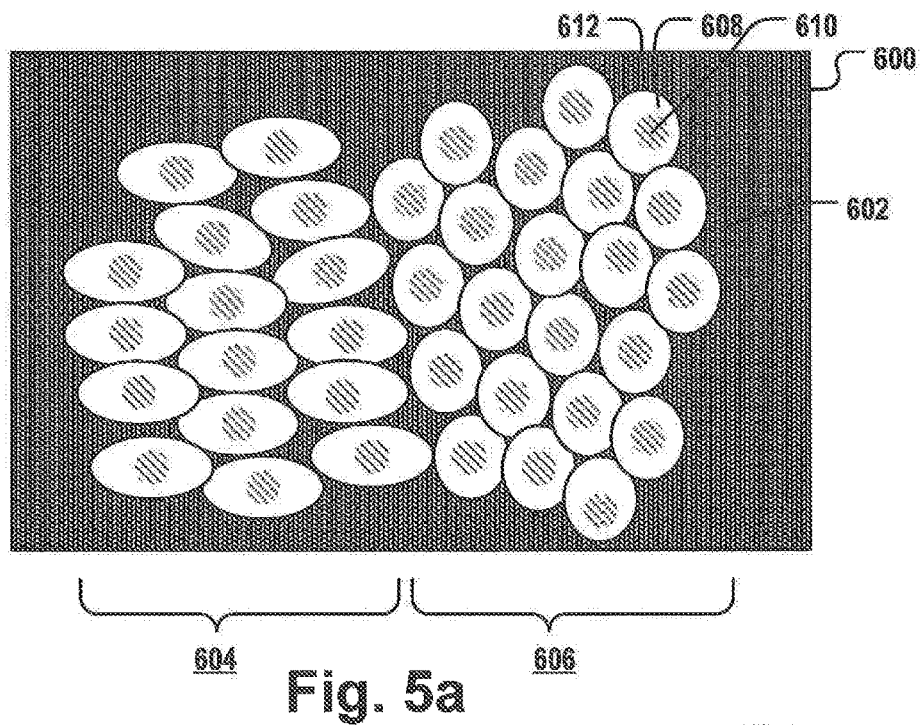
FIGS. 5a-5d depicts multiple biomedical use case scenarios for performing spatial database operations on multiple digital images of an image set.
Figure 5B:
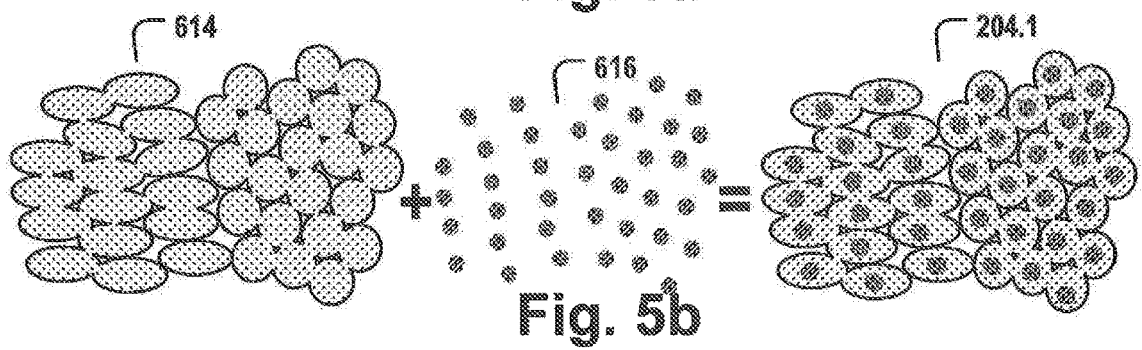

According to one example depicted in FIG. 5b, a generic cell detection approach may compare the areas defined by multiple first polygons 614 respectively representing a cell boundary with the areas defined by multiple second polygons 616 respectively representing a nuclear blob. A spatial database operation "is completely contained in" may be performed for quickly determining if each first polygon comprises a complete second polygon. This operation may be performed for automatically generating a result illustrated as overlay 204.1 that comprises relative location information of two biomedical features. Said result can be used for removing artifacts having been erroneously classified as first polygons representing a cell or as a second polygon representing a nucleus, as a quality criterion could require that each true nucleus is contained in a cell and that each cell must comprise exactly one nucleus. Thus, database operations may be used for increasing the quality of feature extraction operations used in image analysis.

Figure 5C:
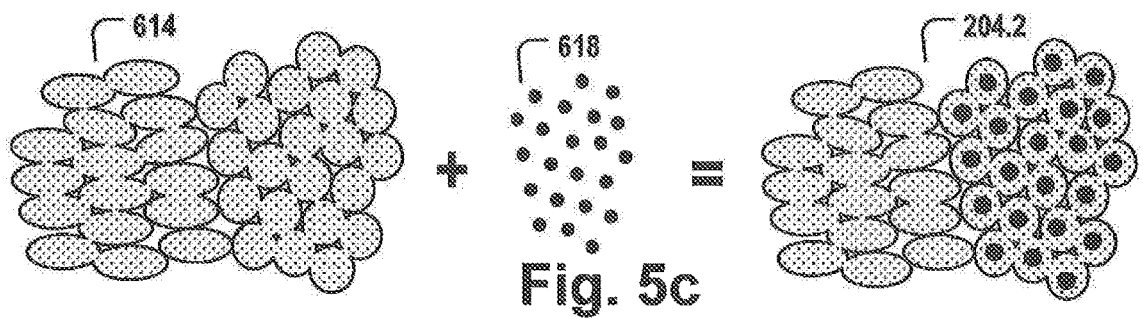

According to a further example depicted in FIG. 5c, the areas defined by multiple first polygons 614 respectively representing a cell boundary are compared with the areas defined by multiple second polygons 618 respectively representing a biomarker being indicative of a cell being a tumor-cell of a particular type. A spatial database operation for selecting all first polygons as tumor cells comprising a second polygon 618 may be performed for quickly identifying all tumor cells in a tissue. This operation may be performed for automatically generating a result illustrated as overlay 204.2 that comprises relative location information of the two biomedical features. Said result can be used for quickly identifying the existence and location of tumor cells in a tissue.

Figure 5D:
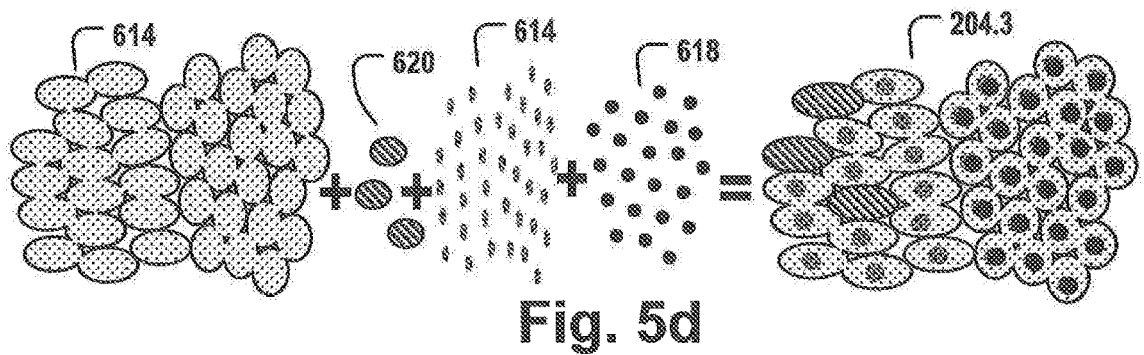

According to a further example depicted in FIG. 5d, it is possible to compare the position information of more than two biomedical features. The location of biomedical features 614 and 616 may be analyzed and compared as described for FIG. 5b. The location of biomedical features 614 and 618 may be analyzed and compared as described for FIG. 5c. The location of biomedical features 614, 620 and 618 may be analyzed and compared as described for FIG. 4, whereby the three polygons 620 can be, for example, immune cells and the polygons 618 can be a biomarker whose presence indicates that a cell is a tumor cell. Moreover, embodiments of the invention may use pre-computed minimum boundary rectangles, polygon areas and/or geometric centers of polygons or polygon aggregates for computing additional relative spatial information, e.g. the size difference of cells of different types, the degree of infiltration of a tissue by cells of another tissue, and the like. Said operations are performed by spatial database operations that can make use of the spatial index created for the spatial data objects e.g. for quickly determining if a spatial object is completely or partially contained in another spatial object, if there exist intersections between two data objects or not.

In addition, statistical evaluations on absolute geometrical information such as density information and on relative geometrical information such as the distance of two biomedical features that compare data of the same patient at different times (before, during or after treatment) or that compare data of different cohorts of patients or healthy persons can be performed by the spatial DBMS or by an image analysis or statistical application program.

The invention claimed is:

1. An image analysis method for analyzing an IHC (immunohistochemical) tissue sample, the method comprising:
   storing, for each of one or more sets of digital images, a set-ID in a spatial database of a spatial DBMS (database management system), the digital images of each digital image set depicting the same or adjacent layers of the IHC tissue sample;
   storing, for each of the digital images, a plurality of spatial data objects in the spatial database in association with the set-ID, each spatial data object being a point, a line, a polygon or a combination thereof and representing a biomedical feature of the tissue sample, the biomedical features of the tissue sample represented by the data objects belonging to at least two different types of biomedical features;
   creating, by the spatial DBMS, at least one spatial index covering the spatial data objects of the digital images contained in the one or more sets, wherein for each of the at least two different types of biomedical features of each of the one or more sets of digital images, a respective spatial index or a partition of the at least one spatial index is created;
   selecting one of the one or more sets of digital images;
   applying, by the spatial DBMS, a spatial database operation on the at least one spatial index for determining the relative positions of spatial data objects of two or more digital images of the selected digital image set;
   providing the relative positions as input for determining the distance and/or relative position of the biomedical features of the tissue sample represented by the spatial data objects of the two or more digital images.

2. The image analysis method of claim 1, each of the spatial data objects being stored as a data record in a respective line of a table of the spatial database.

3. The image analysis method of claim 1, the spatial index being selected from the group comprising:
an R-tree index;
R+ tree index;
R* tree index;
Hilbert R-tree index;
a quadtree index;
a Grid spatial index;
a Z-order index;
an UB-tree index;
X-tree index;
Kd-tree index;
m-tree index;
binary space partitioning (BSP-tree) index.

4. The image analysis method of claim 1, the at least two types being selected from a group comprising: a particular cell type, a particular organelle type, a cell cluster of a particular cluster type, a particular anatomical structure spanning multiple cells, a particular tissue type, a tumor tissue.

5. The image analysis method of claim 1, the further comprising:
automatically identifying one or more of the biological features in some or all of the digital images of the one or more sets, the identification comprising automatically performing a blob extraction and blob classification operation for automatically classifying pixel regions of the digital image representing a biological feature of a particular type; and/or
receiving, by the spatial DBMS, one or more further ones of the biological features in some or all of the digital images of the one or more sets, the received further biological features being pixel regions of the digital image manually classified as representing a biological feature of a particular type;
automatically extracting the spatial data objects from the automatically identified and/or manually classified biomedical features and performing the storing of spatial data object on the extracted spatial data objects.

6. The image analysis method of claim 1, further comprising:
for each of the digital images of each of the one or more sets of digital images, creating a respective spatial index or creating a partition of the at least one spatial index.

7. The image analysis method of claim 1, the method further comprising performing a pre-processing operation before performing the analysis of the relative positions of the spatial data objects, the preprocessing comprising:
automatically pre-computing, by the spatial DBMS, the area size, the geometric center and/or the minimum bounding rectangle of the spatial data objects of the digital images; and
using the precomputed area size, geometric center and/or the minimum bounding rectangle for determining the distance and/or relative position of the biomedical features.

8. The image analysis method of claim 1, the method further comprising:
generating, by an image analysis application program, each of the sets of digital images, the generation comprising performing an image registration operation for registering a plurality of digital images depicting the same or adjacent layers of an IHC tissue sample into a common coordinate system.

9. The image analysis method of claim 8, the generation of at least one of the sets of digital images comprising:
performing a spectral unmixing operation for generating the plurality of digital images depicting the same layer of an IHC tissue sample, each of the digital images of the at least one set corresponding to a different color.

10. The image analysis method of claim 1, wherein set-IDs of multiple sets of digital images and spatial data objects derived from said multiple sets of digital images are stored in the spatial database,
wherein one or more first ones of the digital image sets respectively comprise digital images of a tumor biopsy sample before treatment; and
wherein one or more second ones of the digital image sets respectively comprise digital images of a tumor biopsy sample during treatment; and/or
wherein one or more third ones of the digital image sets respectively comprise digital images of a tumor biopsy sample after treatment.

11. The image analysis method of claim 1,
wherein set-IDs of multiple sets of digital images and spatial data objects derived from said multiple sets of digital images are stored in the spatial database,
wherein fourth ones of the sets of digital images comprise digital images of tissue samples of a first cohort of people who have a particular condition and
wherein fifth ones of the sets of digital images comprise digital images of tissue samples of a second cohort of people who do not have particular condition;
the method comprising:
selecting the fourth and the fifth sets of the digital images and performing, by the spatial DBMS, the analysis on each of the fourth and fifth sets of digital images;
computing a first statistical mean of the relative position of spatial data objects representing two or more different biological features of the digital images in the fourth digital image sets;
computing a second statistical mean of the relative position of spatial data objects representing said two or more different biological features of the digital images in the fifth digital image sets; and
automatically comparing the first and second statistical mean for identifying statistically significant differences between the first and the second cohort of persons.

12. The image analysis method of claim 1, the spatial database operation for analyzing the relative position of the spatial data objects being selected from a group comprising:
determining if a first region of one of the digital images in the selected set is completely contained in a second region of another digital image of the same set;
determining if a first region of one of the digital images in the selected set overlaps with a second region of another digital image of the same set;
determining the spatial distance of a spatial data object representing a biological feature of a first type in one of the digital images in the selected set relative to a spatial data object representing a biological feature of another type in another one of the digital images of the same set;
determining patterns of relative locations of spatial data objects representing a biological feature of a first type in one of the digital images in the selected set relative to the location of spatial data objects representing a biological feature of another type in another one of the digital images of the same set.

13. The image analysis method of claim 1, further comprising:
- computing, by the spatial DBMS, the density of spatial data objects of one or more of the digital images of one or more of the digital image sets; and
- analyzing the computed densities for automatically classifying, by the spatial DBMS or by an image analysis application program, the spatial data objects into one of a plurality of predefined biomedical feature classes.

14. An image analysis system comprising a spatial DBMS (database management system) with a spatial database and comprising a processor, the processor being configured for:
- storing, for each of one or more sets of digital images, a set-ID in a spatial database of a spatial DBMS, the digital images of each digital image set depicting the same or adjacent layers of the IHC (immunohistochemical) tissue sample;
- storing, for each of the digital images, a plurality of spatial data objects in the spatial database in association with the set-ID, each spatial data object being a point, a line, a polygon or a combination thereof and representing a biomedical feature of the tissue sample, the biomedical features of the tissue sample represented by the data objects belonging to at least two different types of biomedical features;
- executing first program routines of the spatial DBMS for creating at least one spatial index covering the spatial data objects of the digital images contained in the one or more sets, wherein for each of the at least two different types of biomedical features of each of the one or more sets of digital images, a respective spatial index or a partition of the at least one spatial index is created;
- receiving a selection of one of the one or more sets of digital images;
- executing second program routines of the spatial DBMS for applying a spatial database operation on the at least one spatial index for determining the relative positions of spatial data objects of two or more digital images of the selected digital image set and for providing the relative positions as input for determining the distance and/or relative position of the biomedical features of the tissue sample represented by the spatial data objects of the two or more digital images.

15. A non-transitory computer-readable storage medium comprising computer readable instructions that, when executed by a processor of an electronic device, cause the electronic device to perform operations including,
- storing, for each of one or more sets of digital images, a set-ID in a spatial database of a spatial DBMS (database management system), the digital images of each digital image set depicting the same or adjacent layers of the IHC (immunohistochemical) tissue sample;
- storing, for each of the digital images, a plurality of spatial data objects in the spatial database in association with the set-ID, each spatial data object being a point, a line, a polygon or a combination thereof and representing a biomedical feature of the tissue sample, the biomedical features of the tissue sample represented by the data objects belonging to at least two different types of biomedical features;
- creating, by the spatial DBMS, at least one spatial index covering the spatial data objects of the digital images contained in the one or more sets, wherein for each of the at least two different types of biomedical features of each of the one or more sets of digital images, a respective spatial index or a partition of the at least one spatial index is created;
- selecting one of the one or more sets of digital images;
- applying, by the spatial DBMS, a spatial database operation on the at least one spatial index for determining the relative positions of spatial data objects of two or more digital images of the selected digital image set;
- providing the relative positions as input for determining the distance and/or relative position of the biomedical features of the tissue sample represented by the spatial data objects of the two or more digital images.

* * * * *